(12) United States Patent
Wormington et al.

(10) Patent No.: US 8,781,070 B2
(45) Date of Patent: Jul. 15, 2014

(54) DETECTION OF WAFER-EDGE DEFECTS

(75) Inventors: Matthew Wormington, Littleton, CO (US); Paul Ryan, Darlington (GB); John Leonard Wall, Durham (GB)

(73) Assignee: Jordan Valley Semiconductors Ltd., Migdal Haemek (IL)

( * ) Notice: Subject to any disclaimer, the term of this patent is extended or adjusted under 35 U.S.C. 154(b) by 212 days.

(21) Appl. No.: 13/570,271

(22) Filed: Aug. 9, 2012

(65) Prior Publication Data

US 2013/0039471 A1  Feb. 14, 2013

Related U.S. Application Data

(60) Provisional application No. 61/522,252, filed on Aug. 11, 2011.

(51) Int. Cl.
*G01N 23/20* (2006.01)

(52) U.S. Cl.
CPC .......... *G01N 23/20* (2013.01); *G01N 2223/646* (2013.01); *G01N 2223/6116* (2013.01)
USPC ............................................. 378/81; 378/87

(58) Field of Classification Search
CPC ............ G01N 23/20; G01N 23/20016; G01N 23/20025; G01N 23/207; G01N 2223/646; G01N 2223/6116
USPC .................... 378/51, 70, 71, 81, 86, 87, 98.12
See application file for complete search history.

(56) References Cited

U.S. PATENT DOCUMENTS

| 2,805,342 A | 9/1957 | Lang |
| 4,242,588 A | 12/1980 | Silk et al. |
| 4,446,568 A | 5/1984 | Williams et al. |
| 4,696,024 A | 9/1987 | Pesch |

(Continued)

FOREIGN PATENT DOCUMENTS

| JP | 3075548 A | 3/1991 |
| JP | 5188019 A | 7/1993 |

(Continued)

OTHER PUBLICATIONS

He, B., "Two-dimensional X-ray Diffraction", pp. 356-359, Published by John Wiley & Sons, Inc., USA, 2009.

(Continued)

*Primary Examiner* — Courtney Thomas
(74) *Attorney, Agent, or Firm* — D. Kligler I.P. Services Ltd.

(57) ABSTRACT

Apparatus for inspection of a disk, which includes a crystalline material and has first and second sides. The apparatus includes an X-ray source, which is configured to direct a beam of X-rays to impinge on an area of the first side of the disk. An X-ray detector is positioned to receive and form input images of the X-rays that are diffracted from the area of the first side of the disk in a reflective mode. A motion assembly is configured to rotate the disk relative to the X-ray source and detector so that the area scans over a circumferential path in proximity to an edge of the disk. A processor is configured to process the input images formed by the X-ray detector along the circumferential path so as to generate a composite output image indicative of defects along the edge of the disk.

20 Claims, 4 Drawing Sheets

(56) References Cited

U.S. PATENT DOCUMENTS

| | | |
|---|---|---|
| 4,725,963 A | 2/1988 | Taylor et al. |
| 4,847,882 A | 7/1989 | Knoth et al. |
| 4,989,226 A | 1/1991 | Woodbury et al. |
| 5,151,588 A | 9/1992 | Kiri et al. |
| 5,340,988 A | 8/1994 | Kingsley et al. |
| 5,373,544 A | 12/1994 | Goebel |
| 5,481,109 A | 1/1996 | Ninomiya et al. |
| 5,530,732 A | 6/1996 | Takemi |
| 5,574,284 A | 11/1996 | Farr |
| 5,619,548 A | 4/1997 | Koppel |
| 5,740,226 A | 4/1998 | Komiya et al. |
| 5,850,425 A | 12/1998 | Wilkins |
| 5,900,645 A | 5/1999 | Yamada |
| 5,923,720 A | 7/1999 | Barton et al. |
| 5,949,847 A | 9/1999 | Terada et al. |
| 5,963,329 A | 10/1999 | Conrad et al. |
| 6,041,098 A | 3/2000 | Touryanski et al. |
| 6,062,084 A | 5/2000 | Chang et al. |
| 6,192,103 B1 | 2/2001 | Wormington et al. |
| 6,226,347 B1 | 5/2001 | Golenhofen |
| 6,226,349 B1 | 5/2001 | Schuster et al. |
| 6,317,483 B1 | 11/2001 | Chen |
| 6,331,890 B1 | 12/2001 | Marumo et al. |
| 6,381,303 B1 | 4/2002 | Vu et al. |
| 6,389,102 B2 | 5/2002 | Mazor et al. |
| 6,453,006 B1 | 9/2002 | Koppel et al. |
| 6,459,763 B1 | 10/2002 | Koinuma et al. |
| 6,504,902 B2 | 1/2003 | Iwasaki et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,574,305 B2 | 6/2003 | Boer et al. |
| 6,625,250 B2 | 9/2003 | Houge |
| 6,639,968 B2 | 10/2003 | Yokhin et al. |
| 6,643,354 B2 | 11/2003 | Koppel et al. |
| 6,665,372 B2 | 12/2003 | Bahr et al. |
| 6,680,996 B2 | 1/2004 | Yokhin et al. |
| 6,711,232 B1 | 3/2004 | Janik |
| 6,718,008 B1 | 4/2004 | He et al. |
| 6,744,850 B2 | 6/2004 | Fanton et al. |
| 6,744,950 B2 | 6/2004 | Aleksoff |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,768,785 B2 | 7/2004 | Koppel et al. |
| 6,771,735 B2 | 8/2004 | Janik et al. |
| 6,782,076 B2 | 8/2004 | Bowen et al. |
| 6,807,251 B2 | 10/2004 | Okanda et al. |
| 6,810,105 B2 | 10/2004 | Nasser-Ghodsi et al. |
| 6,813,338 B2 | 11/2004 | Takata et al. |
| 6,879,051 B1 | 4/2005 | Singh et al. |
| 6,895,075 B2 | 5/2005 | Yokhin et al. |
| 6,898,270 B2 | 5/2005 | Lange et al. |
| 6,937,694 B2 | 8/2005 | Yokoyama et al. |
| 6,947,520 B2 | 9/2005 | Yokhin et al. |
| 6,963,630 B2 | 11/2005 | Umezawa et al. |
| 6,970,532 B2 | 11/2005 | Hayashi et al. |
| 6,987,832 B2 | 1/2006 | Koppel et al. |
| 6,996,208 B2 | 2/2006 | Helming et al. |
| 6,999,557 B2 | 2/2006 | Yamaguchi et al. |
| 7,003,075 B2 | 2/2006 | Miyake et al. |
| 7,035,373 B2 | 4/2006 | Omote |
| 7,062,013 B2 | 6/2006 | Berman et al. |
| 7,068,753 B2 | 6/2006 | Berman et al. |
| 7,076,024 B2 | 7/2006 | Yokhin |
| 7,110,491 B2 | 9/2006 | Mazor et al. |
| 7,113,566 B1 | 9/2006 | Peled et al. |
| 7,116,754 B2 | 10/2006 | Lischka et al. |
| 7,120,227 B2 | 10/2006 | Ozawa et al. |
| 7,120,228 B2 | 10/2006 | Yokhin et al. |
| 7,158,608 B2 | 1/2007 | Kucharczyk |
| 7,213,686 B2 | 5/2007 | Kaufman |
| 7,231,016 B2 | 6/2007 | Berman et al. |
| 7,242,743 B2 | 7/2007 | Fewster |
| 7,242,745 B2 | 7/2007 | He et al. |
| 7,258,485 B2 | 8/2007 | Nakano et al. |
| 7,280,200 B2 | 10/2007 | Plemmons et al. |
| 7,406,153 B2 | 7/2008 | Berman |
| 7,474,732 B2 | 1/2009 | Berman et al. |
| 7,483,513 B2 | 1/2009 | Mazor et al. |
| 7,508,504 B2 | 3/2009 | Jin et al. |
| 7,551,719 B2 | 6/2009 | Yokhin et al. |
| 7,629,798 B2 | 12/2009 | Mallory et al. |
| 7,742,564 B2 | 6/2010 | Parham et al. |
| 8,243,878 B2 | 8/2012 | Yokhin et al. |
| 2003/0123610 A1 | 7/2003 | Okanda et al. |
| 2003/0157559 A1 | 8/2003 | Omote et al. |
| 2005/0023491 A1 | 2/2005 | Young et al. |
| 2009/0116727 A1 | 5/2009 | Jin et al. |
| 2009/0196489 A1* | 8/2009 | Le ................................ 382/148 |
| 2012/0014508 A1 | 1/2012 | Wormington et al. |
| 2012/0140889 A1 | 6/2012 | Wall et al. |
| 2012/0281814 A1 | 11/2012 | Yokhin et al. |

FOREIGN PATENT DOCUMENTS

| | | |
|---|---|---|
| JP | 666741 A | 3/1994 |
| JP | 6258260 A | 9/1994 |
| JP | 6273357 A | 9/1994 |
| JP | 7311163 A | 11/1995 |
| JP | 8-313458 A | 11/1996 |
| JP | 9210663 A | 8/1997 |
| JP | 9-229879 A | 9/1997 |
| JP | 10048398 A | 2/1998 |
| JP | 10160688 A | 6/1998 |
| JP | 10206354 A | 8/1998 |
| JP | 10318949 A | 12/1998 |
| JP | 1114562 A | 1/1999 |
| JP | 11014561 A | 1/1999 |
| JP | 11304728 A | 11/1999 |
| JP | 200088776 A | 3/2000 |
| JP | 2000266698 A | 9/2000 |
| JP | 2000292379 A | 10/2000 |
| JP | 2000314708 A | 11/2000 |
| JP | 200166398 A | 3/2001 |
| JP | 2001153822 A | 6/2001 |
| JP | 2003194741 A | 7/2003 |
| JP | 2003329619 A | 11/2003 |
| JP | 2004257914 A | 9/2004 |
| JP | 2005172830 A | 6/2005 |
| JP | 2005214712 A | 8/2005 |
| JP | 2005265841 A | 9/2005 |
| JP | 2005315742 A | 11/2005 |
| JP | 2005326261 A | 11/2005 |
| JP | 2006317249 A | 11/2006 |
| WO | 2004013867 A2 | 2/2004 |

OTHER PUBLICATIONS

Bowen et al., "X-Ray metrology by Diffraction and Reflectivity," CP550, Characterization and Metrology for ULSI Technology: 2000 International Conference, pp. 570-579, American Institute of Physics, 2001.

Cohen et al., "Characterization of the silicon on insulator film in bonded wafers by high resolution x-ray diffraction", Applied Physics Letters, vol. 75, No. 6, pp. 787-789, Aug. 9, 1999.

Cohen et al., "High-Resolution X-Ray Diffraction for Characterization and Monitoring of Silicon-on-Insulator Fabrication Processes," Journal of Applied Physics, vol. 93, No. 1, pp. 245-250, Jan. 1, 2003.

Goorsky et al., "Grazing Incidence In-plane Diffraction Measurement of In-plane Mosaic with Microfocus X-ray Tubes", Crystal Research and Technology, vol. 37, No. 7, pp. 645-653, year 2002.

Hayashi et al., "Refracted X-Rays Propagating Near the Surface under Grazing Incidence Condition," Spectrochimica Acta, Part B 54, pp. 227-230, year 1999.

Hu et al., "Small angle x-ray scattering metrology for sidewall angle and cross section of nanometer scale line gratings," Journal of Applied Physics, vol. 96, No. 4, pp. 1983-1987, Aug. 15, 2004.

Guerault, H., "Specular reflectivity and off-specular scattering: Tools for roughness investigation", Instituut voor Kern- en Stralingsfysica, Dec. 15, 2000.

(56) References Cited

OTHER PUBLICATIONS

Jones et al., "3-Dimensional Lineshape Metrology Using Small Angle X-ray Scattering", AIP Conference Proceedings, vol. 683, pp. 434-438, Sep. 30, 2003.

Jones et al., "Sub-Nanometer Wavelength Metrology of Lithographically Prepared Structures: A Comparison of Neutron and X-Ray Scattering", Proceedings of SPIE—the International Society for Optical Engineering, Jun. 1, 2003.

Jones et al., "Small Angle X-ray Scattering for Ssub-100 nm Pattern Characterization," Applied Physics Letters, vol. 83, No. 19, pp. 4059-4061, Nov. 10, 2003.

Jordan Valley, "How to Measure SiGe on SOI on BedeMetrixTM Tools", Electronic Materials Conference 2008, USA, Jul. 21, 2008.

Kojima et al., "Structural Characterization of Thin Films by X-ray Reflectivity," Rigaku Journal, vol. 16, No. 2, pp. 31-41, year 1999.

Kozaczek et al., "X-ray Diffraction Metrology for 200mm Process Qualification and Stability Assessment," Advanced Metallization Conference, Canada, Oct. 8-11, 2001.

X-Ray Optical Systems, Inc., "Monolithic Polycapillary Lens Information", Albany, USA, Dec. 29, 1998.

Wu et al., "Substepping and its Application to HST Imaging", Astronomical Data Analysis Software and Systems VII ASP Conference Series, vol. 145, pp. 82-85, year 1998.

Naudon et al., "New Apparatus for Grazing X-ray Reflectometry in the Angle-Resolved Dispersive Mode," Journal of Applied Crystallography, vol. 22, pp. 460-464, year 1989.

Neissendorfer et al., "The Energy-Dispersive Reflectometer/Diffractometer at BESSY-I", Measurement Science Technology, vol. 10, pp. 354-361, IOP Publishing Ltd., year 1999.

Parrill et al., "GISAXS—Glancing Incidence Small Angle X-ray Scattering," Journal de Physique IV, vol. 3, pp. 411-417, Dec. 1993.

Powell et al., "X-ray Diffraction and Reflectivity Characterization of SiGe Superlattice", Semiconductor Science Technology Journal, vol. 7, pp. 627-631, year 1992.

Di Fonzo et al., "Non-Destructive Determination of Local Strain with 100-Nanometre Spatial Resolution," Nature, vol. 403, pp. 638-640, Feb. 10, 2000.

Ulyanenkov, A., "Introduction to High Resolution X-Ray Diffraction," Workshop on X-ray characterization of thin layers, Uckley, May 21-23, 2003.

Authier, A., "Dynamical Theory of X-Ray Diffraction", International Union of Crystallography, Monographs on Crystallography 11, revised edition, pp. 101-102, Oxford University Press 2005.

Wiener et al., "Characterization of Titanium Nitride Layers by Grazing- Emission X-Ray Fluorescence Spectrometry", Applied Surface Science, vol. 125, pp. 129-136, Elsevier Science BV 1998.

Woitok et al., "Towards Fast Reciprocal Space Mapping," JCPDS—International Centre for Diffraction Data, Advances in X-ray Analysis, vol. 48, pp. 165-169, year 2005.

Oxford Instruments Inc., Series 5000 Model XTF5011 X-Ray Tube Datasheet, Scotts Valley, USA, Jun. 28, 2000.

Japanese Patent Application # 2003549898 Official Action dated Jun. 7, 2010.

U.S. Appl. No. 09/941,723 Official Action dated Apr. 4, 2005.

U.S. Appl. No. 10/946,426 Official Action dated Feb. 6, 2006.

U.S. Appl. No. 11/018,352 Official Action dated Feb. 8, 2006.

U.S. Appl. No. 11/018,352 Official Action dated Oct. 24, 2005.

U.S. Appl. No. 11/200,857 Official Action dated Aug. 11, 2008.

U.S. Appl. No. 11/200,857 Official Action dated Aug. 27, 2007.

U.S. Appl. No. 11/200,857 Official Action dated Mar. 11, 2008.

U.S. Appl. No. 11/389,490 Official Action dated May 1, 2008.

U.S. Appl. No. 11/487,433 Official Action dated May 29, 2008.

U.S. Appl. No. 61/328,645, filed Apr. 28, 2010.

Japanese Patent Application # 2005274293 Official Action dated Dec. 21, 2010.

Japanese Patent Application # 2005273641 Official Action dated Oct. 28, 2010.

Pesek et al., "Lattice Misfit and Relative Tilt of Lattice Planes in Semiconductor Heterostructures", Semiconductor Science and Technology Journal, vol. 6, pp. 705-708, IOP Publishing Ltd 1991.

Japanese Patent Application # 2006114489 Official Action dated Nov. 30, 2010.

Japanese Patent Application # 2006114489 Official Action dated Jun. 14, 2011.

Japanese Patent Application # 2006194756 Official Action dated Jul. 26, 2011.

U.S. Appl. No. 12/683,436 Office Action dated Jan. 23, 2012.

Korean Patent Application # 10-2005-0083542 Office Action dated Feb. 15, 2012.

"Computer-Controlled X-ray Topographic Imaging System", Rigaku Journal, vol. 1, No. 1, pp. 23-24, year 1984.

Photonic Science Ltd., "X-Ray FDI Camera", pp. 1-5, Apr. 28, 2011.

\* cited by examiner

DETECTION OF WAFER-EDGE DEFECTS

CROSS-REFERENCE TO RELATED APPLICATION

This application claims the benefit of U.S. Provisional Patent Application 61/522,252, filed Aug. 11, 2011, which is incorporated herein by reference.

FIELD OF THE INVENTION

The present invention relates generally to X-ray diffraction imaging, and specifically to methods and apparatus for detecting defects at the edge of a sample using X-rays.

BACKGROUND

Silicon wafer edges are very frequently damaged during shipping, handling and processing. For example, mechanical damage from wafer handling can cause cracks, which can lead to wafer breakage, as well as chips that result in the creation of particles. Thermal cycling can cause delamination of thin films or plastic deformation of the wafer through slip, which can lead to problems with overlay alignment required for advanced lithography. These sorts of wafer-edge defects, if undetected, can have catastrophic consequences, and may lead to loss of an entire wafer in late stages of processing.

Various methods have been developed for detection of wafer-edge defects. For example, U.S. Pat. No. 6,062,084 describes an apparatus in which an ultrasonic detection unit is used to detect crazing or micro-cracks in a wafer edge, while a laser detection unit is used for detecting cracks in the wafer edge. As another example, U.S. Pat. No. 7,508,504 describes an automatic wafer edge inspection and review system, in which a light diffuser with a plurality of lights provides uniform diffuse illumination of a substrate. An optic and imaging system exterior of the light diffuser is used to inspect the plurality of surfaces of the substrate including specular surfaces. The optic can be rotated radially relative to a center point of the substrate edge to allow for focused inspection of all surfaces of the substrate edge.

X-ray diffraction imaging (XRDI), also known as X-ray topography, has been used to detect crystalline defects based on local changes in the diffracted X-ray intensity. For example, U.S. Pat. No. 6,782,076, whose disclosure is incorporated herein by reference, describes an X-ray topographic system, comprising an X-ray generator producing a beam of X-rays impinging on a limited area of a sample such as a silicon wafer. A solid-state detector is positioned to intercept the beam after transmission through or reflection from the sample and produces a digital image of the area on which the X-rays impinge. Relative stepping motion between the X-ray generator and the sample produces a series of digital images, which are combined together. In optional embodiments, an X-ray optic is interposed to produce a parallel beam to avoid image doubling, or the effect of image doubling is removed by software.

SUMMARY

Embodiments of the present invention that are described hereinbelow provide improved methods and apparatus for detection of defects at the edge of a substrate, such as a silicon wafer, with high sensitivity and throughput.

There is therefore provided, in accordance with an embodiment of the present invention, apparatus for inspection of a disk, which includes a crystalline material and has first and second sides. The apparatus includes an X-ray source, which is configured to direct a beam of X-rays to impinge on an area of the first side of the disk. An X-ray detector is positioned to receive and form input images of the X-rays that are diffracted from the area of the first side of the disk in a reflective mode. A motion assembly is configured to rotate the disk relative to the X-ray source and detector so that the area scans over a circumferential path in proximity to an edge of the disk. A processor is configured to process the input images formed by the X-ray detector along the circumferential path so as to generate a composite output image indicative of defects along the edge of the disk.

The defects may include cracks in the disk. Typically, the processor is configured to form the composite image in a coordinate system defined by a radial distance and an azimuth relative to a center of the disk. In the disclosed embodiments, the disk includes a semiconductor wafer.

In some embodiments, the X-ray source and X-ray detector respectively include a first X-ray source and a first X-ray detector positioned opposite the first side of the disk, and the first X-ray detector forms first input images of a first area on the first side of the disk, and the apparatus includes a second X-ray source, which is configured to direct X-rays to impinge on a second area on the second side of the disk, and a second X-ray detector, which is positioned to receive and form second input images of the X-rays that are diffracted from the second area. Typically, a projection of the first area onto the second side of the disk overlaps the second area, and the processor is configured to jointly process the first and second input images of the overlapping first and second areas. The processor may be configured to compare the first and second input images so as to detect cracks passing through the disk.

Typically, the X-ray source and the X-ray detector are positioned so that the X-ray detector receives Bragg reflections from a crystal plane that is parallel to within $\pm 2°$ to the first side of the disk. The X-ray source and the X-ray detector may be symmetrically positioned at equal elevations angles relative to the disk, or they may be non-symmetrically positioned at different, respective elevations angles relative to the disk.

There is also provided, in accordance with an embodiment of the present invention, a method for inspection of a disk, which includes a crystalline material and has first and second sides. The method includes directing a beam of X-rays to impinge on an area of the first side of the disk. Input images are formed of the X-rays that are diffracted from the area of the first side of the disk in a reflective mode. The disk is rotated so that the area on which the beam of X-rays impinges scans over a circumferential path in proximity to an edge of the disk. The input images formed along the circumferential path are processed so as to generate a composite output image indicative of defects along the edge of the disk.

The present invention will be more fully understood from the following detailed description of the embodiments thereof, taken together with the drawings in which:

DETAILED DESCRIPTION OF EMBODIMENTS

Figure 1:
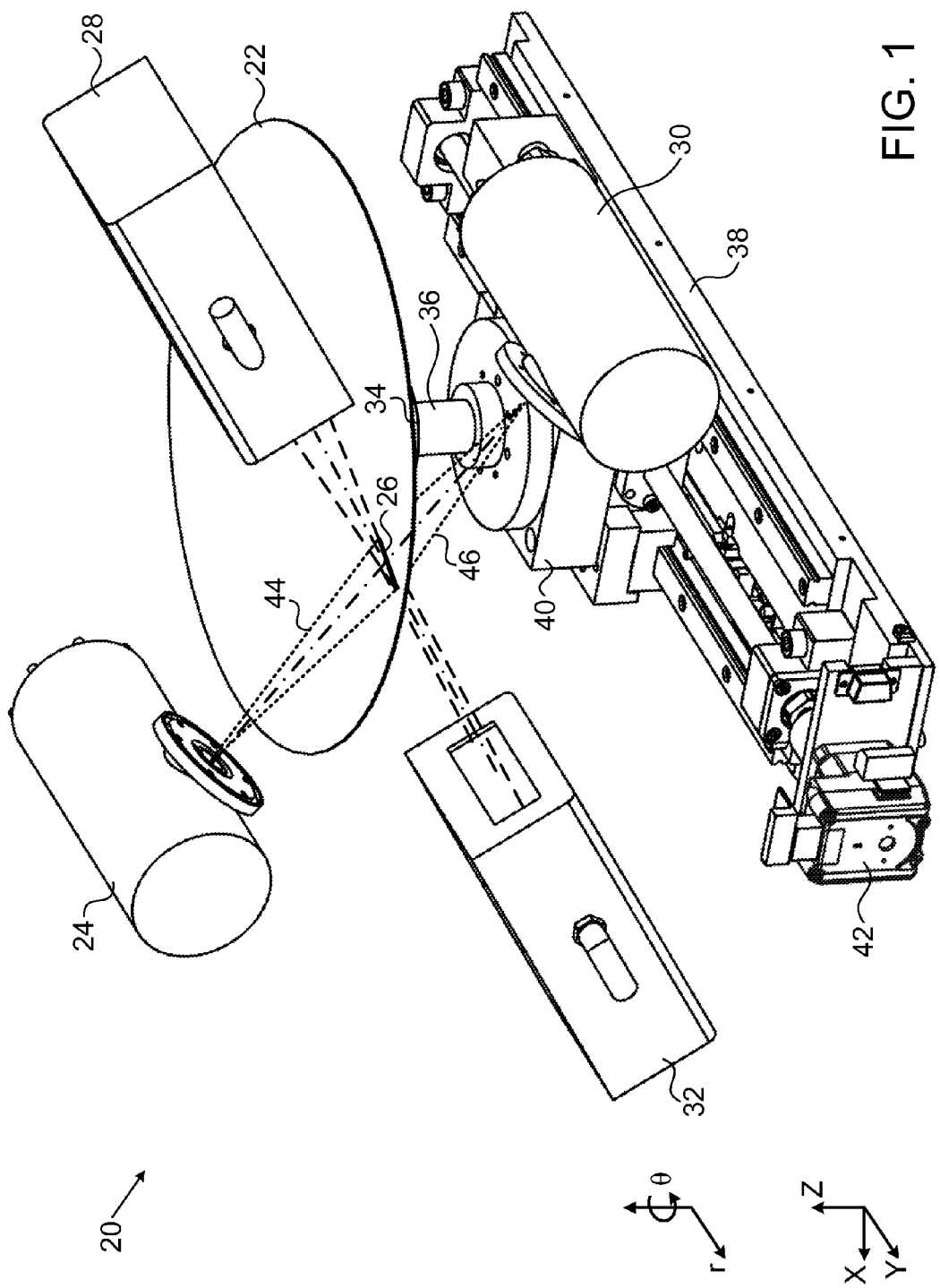
FIG. 1 is a schematic, pictorial view of a system for detection of wafer-edge defects, in accordance with an embodiment of the invention.

Embodiments of the present invention that are described hereinbelow provide apparatus and methods for detection of defects at the edge of a disk of crystalline material, such as a semiconductor wafer. These embodiments apply the principles of X-ray topography that are described, for example, in the above-mentioned U.S. Pat. No. 6,782,076 in a novel manner that enhances the sensitivity and throughput of detection. The techniques described herein are particularly effective in detecting cracks at the wafer edge and can be used to identify cracks that are likely to lead to breakage in later processing stages, such as rapid thermal annealing.

In the disclosed embodiments, inspection apparatus comprises an X-ray source, which directs a beam of X-rays to impinge on an area of a crystalline disk. An X-ray detector, which is positioned at an appropriate angle on the same side of the disk as the source, receives the X-rays that are diffracted from the irradiated area in a reflective mode and forms a diffraction image of the area. Typically, the source and detector are positioned symmetrically, at equal elevation angles, chosen so that the detector receives Bragg reflections from a horizontal crystal plane (parallel to the surface of the disk), but other angular arrangements can alternatively be used to image Bragg reflections from other crystal planes. As long as the irradiated area is defect-free, the X-rays will diffract uniformly from the desired crystal plane, and the image will be featureless. Defects will appear as features in the diffraction image, due to deviations of the crystal planes in the vicinity of the defect.

A motion assembly rotates the disk relative to the X-ray source and detector so that the irradiated area scans over a circumferential path in proximity to the edge of the disk. A processor receives and processes the input images formed by the X-ray detector along the circumferential path and generates a composite output image, showing the defects along the edge of the disk. Unlike X-ray topography systems that are known in the art, this composite image is typically generated in a polar coordinate system, in which one axis corresponds to the radial distance from the center of the disk, and the other axis corresponds to the azimuth relative to the center of the disk.

In some embodiments, a first X-ray source and detector are positioned on one side of the disk, while a second X-ray source and detector are positioned on the other side. The two source/detector pairs simultaneously form diffraction images of respective areas on opposite sides of the disk in proximity to the edge. Typically, the sources and detectors are arranged so that the areas that they irradiate and image overlap, i.e., the projection of the area imaged by the first source/detector pair onto the other side of the disk overlaps the area imaged by the second source/detector pair. The processor jointly processes the images of the overlapping areas on the two sides of the disk and is thus able to detect defects, such as cracks, that pass through the disk. Deep defects of this sort pose a particular risk of subsequent catastrophic failure.

Figure 2:
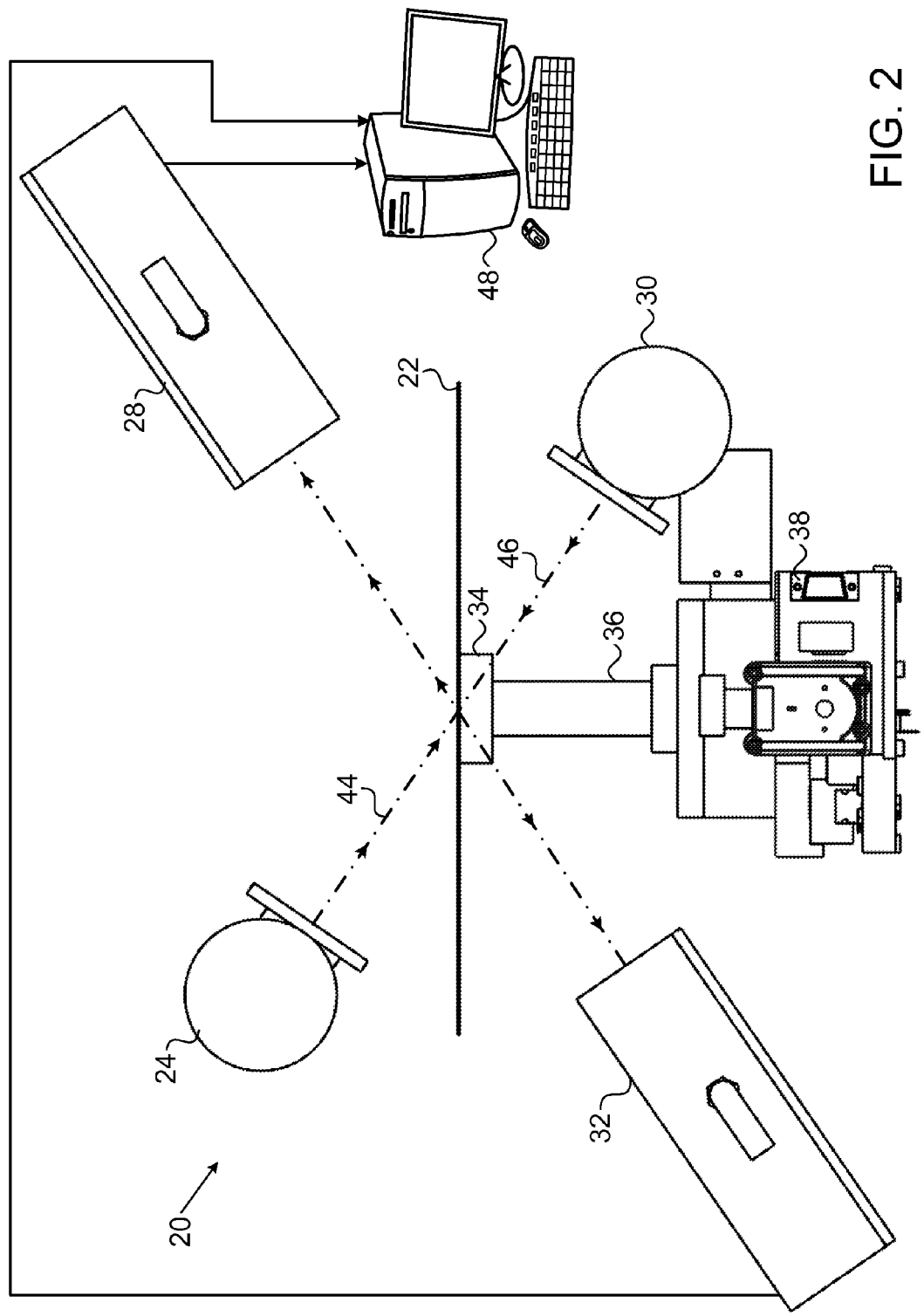
FIG. 2 is a schematic side view of the system of FIG. 1.

Reference is now made to FIGS. 1 and 2, which schematically illustrate a system 20 for detection of defects at the edge of a crystalline disk, such as a semiconductor wafer 22, in accordance with an embodiment of the invention. An X-ray source 24 irradiates an area 26 on the upper surface of wafer 22 with an X-ray beam 44, and an X-ray detector 28 receives the X-rays diffracted from the area in reflective mode. Optionally, a second X-ray source 30 irradiates an area overlapping area 26 on the lower surface of wafer 22 with an X-ray beam 46, and a second X-ray detector 32 receives the X-rays diffracted from this area on the lower surface. In the pictured configuration, sources 24, 26 and detectors 28, 30 are positioned symmetrically at approximately equal elevation angles relative to the wafer surface. The elevation angles are chosen to satisfy the Bragg condition for X-ray diffraction from the horizontal crystal plane in wafer 22, i.e., the plane that is approximately parallel to the wafer surface. (The term "approximately parallel," in the context of the present patent application, means parallel to with ±2°.

Wafer 22 is mounted on a chuck 34 at the top of a spindle 36 of a motion assembly 38. The motion assembly include a rotational drive 40, which rotates spindle 36 about its axis, and a translational drive 42, which translates the spindle linearly, in a radial direction relative to the center of wafer 22. Rotation of spindle 36 by drive 40 corresponds to changing the azimuth θ of area 26, while translation by drive 42 corresponds to changing the radial coordinate r. Motion assembly 38 is thus able to scan area 26 in a circumferential path around the edge of wafer 22, at one or more different values of r.

A processor 48 receives input images, in the form of electrical signals or digital values, that are captured by detectors 28 and 32 in the course of a circumferential scan, and combines these input images to generate a composite output image indicative of defects along the edge of wafer 22. (The composite image can be generated in real time, during inspection, or afterwards based on a set of stored input images.) Typically, processor 48 comprises a general-purpose computer, which has suitable input and output circuits and is programmed in software to carry out the image processing functions described herein. Alternatively or additionally, at least some of these functions may be carried out by hardware logic circuits.

The composite image may combine the overlapping input images provided by the two source/detector pairs on opposite sides of wafer 22. The use of two such source/detector pairs provides enhanced detection capabilities with respect to certain types of defects. Alternatively, system 20 may comprise only a single pair of X-ray source and detector, on one side of wafer 22 (either upper or lower), or only a single such pair may be active in certain inspection configurations, in which case processor 48 generates the composite image based on input images from only one side of the wafer. As a further alternative, system 20 may comprise one or more additional source/detector pairs (not shown) at other azimuthal locations, which may operate simultaneously with the source/detector pairs shown in the figures in order to enhance throughput.

X-ray sources 24 and 30 in this embodiment comprise X-ray tubes with a small emission spot size, typically on the order of 100 μm or less. For example, the Apogee™ tube produced by Oxford Instruments, X-ray Technologies Inc. (Scotts Valley, Calif.) is suited for this purpose. Beams 44 and 46 produced by the X-ray sources are typically divergent, polychromatic X-ray beams. The beams may desirably have an angular divergence of at least 1° in order to permit diffraction imaging from wafers in which the diffraction planes are not exactly parallel to the surface. The X-ray beam typically contains the $K\alpha 1$, $K\alpha 2$ and Kb characteristic radiation of the Cu anode of the X-ray tube, as well as continuous radiation (Bremsstrahlung). The $K\alpha 1$ and $K\alpha 2$ emissions are the most intense with an intensity ratio of 1:2, while the other emissions are much less intense. Alternatively or additionally, other anode types and X-ray emission lines may be used in sources 24 and 30.

Detectors 28 and 32 output electric signals that are indicative of received X-ray intensity in a two-dimensional pixel array. For this purpose, the detectors typically comprise arrays of X-ray sensor elements, such as CCD or CMOS sensor arrays, with a resolution of 100 µm or less. For example, detectors 28 and 32 may comprise FDI2 cameras produced by Photonic Science Ltd. (Robertsbridge, UK), which includes a 1392×1040 pixel sensor array. This sensor array can be configured to detect X-rays over active areas ranging from 4.4×3.5 mm² (3.4 µm optical pixel) to 39×31 mm² (30 µm pixel), depending on the desired field of view and resolution.

The spatial resolution d of the images produced by system 20 is given by the following equation:

$$d = hb/a$$

wherein a is the source distance from area 26, b is the detector distance, and h is the source spot size. Using the Apogee X-ray source (which has a spot size of 50 µm) with a source distance of 50 mm, and a detector distance of 25 mm, system 20 can reach a minimum resolution of 25 µm.

When wafer 22 is stationary, the K$\alpha$1 and K$\alpha$2 radiation components in beams 44 and 46 will image slightly different parts of the wafer surface, since they satisfy the Bragg diffraction condition at slightly different angles. As a result, a near-surface defect will be imaged by the K$\alpha$1 and K$\alpha$2 radiation at slightly different wafer azimuths, and this phenomenon may lead to some broadening or doubling of the defect images. It is possible to remove the contribution made by the K$\alpha$2 and other less intense radiation lines by image processing, for example, by subtracting half the diffracted intensity from the image, or by selecting image signals from only a sub-region of the detector.

Figure 3:
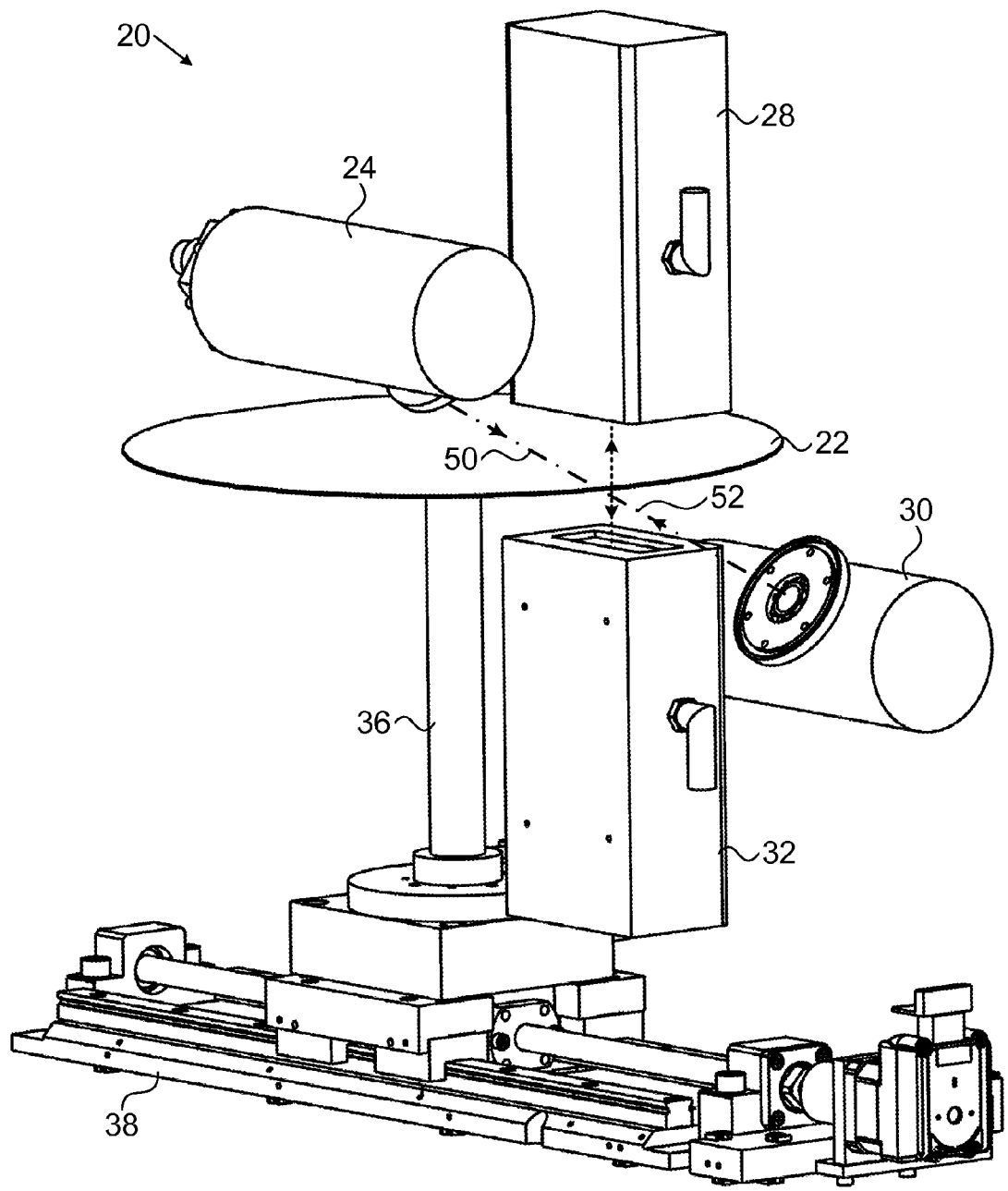
FIG. 3 is a schematic, pictorial view of a system for detection of wafer-edge defects, in accordance with another embodiment of the invention.

FIG. 3 is a schematic, pictorial view of system 20, in accordance with an alternative embodiment of the invention. X-ray sources 24, 30 and detectors 28, 32 are typically held by adjustable mounts (not shown), as are known in the art, which enable their respective elevations to be adjusted while maintaining their common orientation toward the same area 26 on wafer 22. Such mounts may be controlled manually or automatically. They are used, for example, in setting the X-ray sources and detectors in FIGS. 1 and 2 to symmetrical elevations at the appropriate Bragg angle for reflective diffraction from the horizontal crystal plane of wafer 22. In FIG. 3, on the other hand, the elevation angle of detectors 28 and 32 is adjusted, and typically the elevation angle of sources 24 and 30 is adjusted as well, so that the source and detector elevations are non-symmetrical. This non-symmetrical angular configuration may be useful in detecting diffraction at low angles that cannot readily be imaged using a symmetrically-positioned X-ray source and detector and in detecting certain types of defects that are less clearly visible in the symmetrical configuration of FIGS. 1 and 2.

Figure 4:
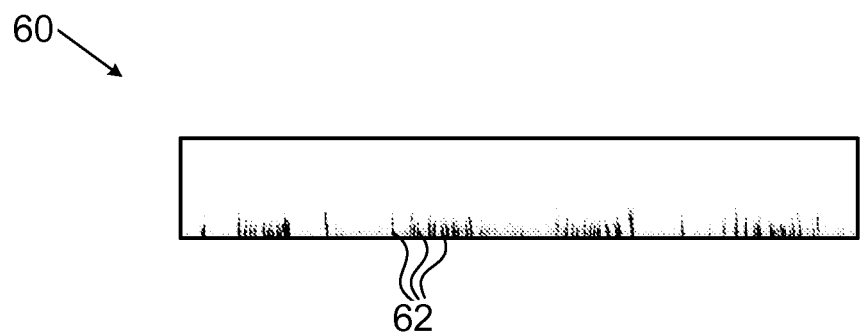
FIG. 4 is a schematic representation of a composite X-ray image of a wafer edge, in accordance with an embodiment of the invention.

FIG. 4 is a schematic representation of a composite X-ray image 60 of a wafer edge, in accordance with an embodiment of the invention. Processor 48 creates this image by stitching together the input images provided by detectors 28 and 32 at different values of azimuth ($\theta$) and possibly different values of radial position (r). The input images were captured using the 004 reflection from a Si(001) wafer and include both the K$\alpha$1 and K$\alpha$2 radiation lines. The acquisition time of each input image was 0.17 sec, and the detector pixel size was 70.5 µm. The horizontal (X) axis in image 60 corresponds to azimuth, while the vertical (Y) axis corresponds to radial position. The gray scale of image 60 is reversed for visual clarity, so that dark stripes 62 correspond to locations of strong diffraction, typically corresponding to defects in the wafer.

The equations used to transform between wafer coordinates (r,$\theta$) and pixel coordinates (x,y) in image 60 are expressed as follows:

$$x = (\theta - \theta_0)/dx$$

$$y = (r - r_0)/dy$$

wherein $(r_0, \theta_0)$ is the origin expressed in wafer coordinates, and dx and dy are the horizontal and vertical dimensions, respectively, of the pixels in the X-ray detector.

Processor 48 acquires a series of input diffraction images at different azimuths as wafer 22 is rotated on spindle 36 in either a continuous or step-wise motion. These images may then be saved to a disk file, for example as an 8-bit, grayscale video file, which may be created using a lossless compression codec to save disk space, together with the respective reference coordinates (r,$\theta$) of each image. (Alternatively, as noted earlier, the input images may be processed in real time.) The processor stitches these input images together over all or a part of the wafer circumference. For example, the following stitching algorithm may be used:

1. Create a 32-bit grayscale image with dimensions sufficient to store a composite image of the entire wafer edge.
2. Read the origin $(r_0, \theta_0)$ of the wafer coordinates and the X-ray detection pixel sizes dx and dy from a disk file.
3. Read in an input diffraction image and its associated reference coordinates (r,$\theta$).
4. Transform the input image coordinates to the coordinate system of the composite image, as given by the equations above.
5. Select the part of the input image (the region of interest—ROI) that is to be incorporated into the composite image.
6. Subtract any background intensity from the input image. This background can include the contribution of the K$\alpha$2 radiation, as noted earlier.
7. Add the intensity image within the ROI at the appropriate location to the composite image created in step 1.
8. Repeat steps 3-7 until all input images have been read and processed.
9. Convert the 32-bit image to an 8-bit image by selecting a region of intensity values of interest and scaling these to the value range 0 to 255.
10. Save the final 8-bit wafer-edge image to disk using a lossless compression format.

Alternatively or additionally, other methods of image processing that are known in the art may be used to stitch together the input images.

If wafer 22 is not perfectly aligned relative to the rotation axis of spindle 36, the apparent radius measured at detectors 28 and 32 will vary slightly as the wafer rotates. This variation may lead to a wavy image, rather than the straight image of the wafer edge that is shown in FIG. 4. To produce a straight, accurate image of the wafer edge under these circumstances, processor 48 may compute and apply a suitable geometrical transformation to correct the input images. One method that can be used to compute and apply such a transformation is described, for example, in the above-mentioned U.S. Provisional Patent Application 61/522,252.

Figure 5:
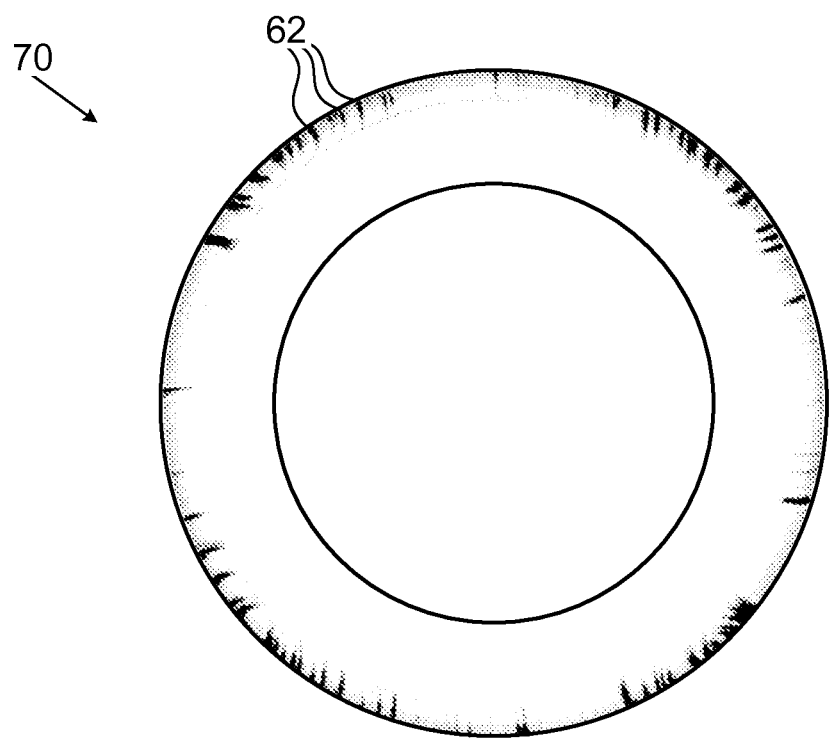
FIG. 5 is a schematic representation of a reconstructed X-ray image of a wafer edge, in accordance with an embodiment of the invention.

FIG. 5 is a schematic representation of a reconstructed X-ray image 70 of the edge of wafer 22, in accordance with an embodiment of the invention. Here the Cartesian coordinates used in the image of FIG. 4 have been transformed geometrically back to polar coordinates in order to give a reconstructed image corresponding in shape and form to the actual wafer edge.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for inspection of a disk, which includes a crystalline material and has first and second sides, the apparatus comprising:
   an X-ray source, which is configured to direct a beam of X-rays to impinge on an area of the first side of the disk;
   an X-ray detector, which is positioned to receive and form input images of the X-rays that are diffracted from the area of the first side of the disk in a reflective mode;
   a motion assembly, which is configured to rotate the disk relative to the X-ray source and detector so that the area scans over a circumferential path in proximity to an edge of the disk; and
   a processor, which is configured to process the input images formed by the X-ray detector along the circumferential path so as to generate a composite output image indicative of defects along the edge of the disk.

2. The apparatus according to claim 1, wherein the defects comprise cracks in the disk.

3. The apparatus according to claim 1, wherein the processor is configured to form the composite image in a coordinate system defined by a radial distance and an azimuth relative to a center of the disk.

4. The apparatus according to claim 1, wherein the X-ray source and X-ray detector respectively comprise a first X-ray source and a first X-ray detector positioned opposite the first side of the disk, and the first X-ray detector forms first input images of a first area on the first side of the disk, and
   wherein the apparatus comprises a second X-ray source, which is configured to direct X-rays to impinge on a second area on the second side of the disk, and a second X-ray detector, which is positioned to receive and form second input images of the X-rays that are diffracted from the second area.

5. The apparatus according to claim 4, wherein a projection of the first area onto the second side of the disk overlaps the second area, and wherein the processor is configured to jointly process the first and second input images of the overlapping first and second areas.

6. The apparatus according to claim 5, wherein the processor is configured to compare the first and second input images so as to detect cracks passing through the disk.

7. The apparatus according to claim 1, wherein the X-ray source and the X-ray detector are positioned so that the X-ray detector receives Bragg reflections from a crystal plane that is parallel to within ±2° to the first side of the disk.

8. The apparatus according to claim 7, wherein the X-ray source and the X-ray detector are symmetrically positioned at equal elevations angles relative to the disk.

9. The apparatus according to claim 7, wherein the X-ray source and the X-ray detector are non-symmetrically positioned at different, respective elevations angles relative to the disk.

10. The apparatus according to claim 1, wherein the disk comprises a semiconductor wafer.

11. A method for inspection of a disk, which includes a crystalline material and has first and second sides, the method comprising:
    directing a beam of X-rays to impinge on an area of the first side of the disk;
    forming input images of the X-rays that are diffracted from the area of the first side of the disk in a reflective mode;
    rotating the disk so that the area on which the beam of X-rays impinges scans over a circumferential path in proximity to an edge of the disk; and
    processing the input images formed along the circumferential path so as to generate a composite output image indicative of defects along the edge of the disk.

12. The method according to claim 11, wherein the defects comprise cracks in the disk.

13. The method according to claim 11, wherein processing the input images comprises forming the composite image in a coordinate system defined by a radial distance and an azimuth relative to a center of the disk.

14. The method according to claim 11, wherein directing the beam of X-rays comprises directing first and second beams of the X-rays to impinge respectively on first and second areas on the first and second sides of the disk, and
    wherein forming the input images comprises capturing, in the reflective mode, first input images of the X-rays that are diffracted from the first area and second input images of the X-rays that are diffracted from the second area.

15. The method according to claim 14, wherein a projection of the first area onto the second side of the disk overlaps the second area, and wherein processing the input images comprises jointly processing the first and second input images of the overlapping first and second areas.

16. The method according to claim 15, wherein jointly processing the first and second input images comprises comparing the first and second input images so as to detect cracks passing through the disk.

17. The method according to claim 11, wherein directing the beam of X-rays and forming the X-ray images comprise irradiating the area and detecting the diffracted X-rays using a source and detector positioned so as to detect Bragg reflections from a crystal plane that is parallel to within ±2° to the first side of the disk.

18. The method according to claim 17, wherein the source and the detector are symmetrically positioned at equal elevations angles relative to the disk.

19. The method according to claim 17, wherein the source and the detector are non-symmetrically positioned at different, respective elevations angles relative to the disk.

20. The method according to claim 11, wherein the disk comprises a semiconductor wafer.

* * * * *